United States Patent [19]

Zupancic et al.

[11] Patent Number: 5,241,097

[45] Date of Patent: Aug. 31, 1993

[54] PROCESS FOR THE PREPARATION OF CYCLIC SILOXANE

[75] Inventors: Joseph J. Zupancic, Bensenville; Jeffrey P. Conrad, Chicago, both of Ill.

[73] Assignee: Allied-Signal Inc., Morristown, N.J.

[21] Appl. No.: 994,005

[22] Filed: Dec. 21, 1992

[51] Int. Cl.$^5$ .................................... C07F 7/08
[52] U.S. Cl. ..................................... 556/460; 556/451
[58] Field of Search ................................. 556/451, 460

[56] References Cited

U.S. PATENT DOCUMENTS

| | | | |
|---|---|---|---|
| 2,741,630 | 4/1956 | Reed et al. | 556/460 X |
| 3,358,009 | 12/1967 | Ostrozynski | 556/460 X |
| 3,432,538 | 3/1969 | Curry | 556/460 |
| 3,484,468 | 12/1989 | Curry et al. | 260/448.2 |
| 3,714,213 | 1/1973 | Miller et al. | 260/448.25 |
| 3,763,212 | 10/1973 | McEntee et al. | 260/448.25 |
| 4,060,537 | 11/1977 | Maass et al. | 260/448.2 |
| 4,329,483 | 5/1982 | Speier | 556/460 |
| 4,366,324 | 12/1982 | Habata et al. | 556/460 |
| 4,772,737 | 9/1988 | Lartigue-Peyrow et al. | 556/460 |
| 4,895,967 | 1/1990 | Crivello et al. | 556/451 |

FOREIGN PATENT DOCUMENTS 834711 9/1957 United Kingdom ................ 556/460

OTHER PUBLICATIONS

Derivatives of the Methylchlorosilanes, V. Polysiloxanes From Methyldichlorosilane by Robert O. Sauer, W. J. Scheiber and Stuart D. Brewer, JACS, 68 (1976).

Primary Examiner—Paul F. Shaver
Attorney, Agent, or Firm—Michael U. Lee; Gerhard H. Fuchs

[57] ABSTRACT

This invention relates to an improved, high-yield process for producing cyclic siloxane in a biphasic reaction solvent mixture comprising an alkane, an alcohol and water.

18 Claims, No Drawings

PROCESS FOR THE PREPARATION OF CYCLIC SILOXANE

BACKGROUND OF THE INVENTION

1. Field of the Invention

The present invention relates to a process for preparing cyclic siloxane, particularly from alkylhalosilanes or alkylalkoxysilanes.

2. Description of the Prior Art

Cyclic siloxanes are generally produced by hydrolyzing alkyldichlorosilanes which results in a mixture of cyclic siloxanes and linear polysiloxanes of various molecular weight. The preparation of cyclic methylsiloxanes utilizing methyldichlorosilane in a solvent system based on diethylether and crushed ice is disclosed by Sauer et al., J. Am. Chem. Soc., vol. 68, 962 (1946). The yield of the process is reported to be 56.7% with the remaining 43.3% being linear polysiloxane. In Curry U.S. Pat. No. 3,484,468 to Curry, a process for producing cyclic methylpolysiloxanes by hydrolysis of dichloromethylsilane in a solvent mixture of a tertiary alcohol and benzene is disclosed. The best yield of the process is reported to be 66% cyclosiloxanes and 34% linear polysiloxanes. In U.S. Pat. No. 3,763,212 to McEntee et al., a process for preparing cyclic sym-polyalkylpolyalkenylpolysiloxane in a mixture of water and a water soluble aliphatic alcohol or aliphatic ketone is disclosed. The reference teaches that the ketone and alcohol must be completely soluble in water.

Cracking linear polysiloxanes at an elevated temperature in the presence of a catalyst is an alternative process for the production of cyclic siloxanes. However, the cracking process has not been widely utilized since the process must proceed from an intermediate polysiloxane and is energy intensive. Illustrative processes are disclosed in Miller et al. U.S. Pat. No. 3,714,213 to Miller eta l. and 4,895,967to Crivello et al.

This invention provides an improved process for producing cyclic siloxanes in high yield and with low energy consumption.

SUMMARY OF THE INVENTION

There is provided in accordance with the present invention an improved, high-yield hydrolysis process for producing cyclic siloxanes which comprises the steps of gradually adding a functional alkylsilane to a well-blended biphasic reaction solvent mixture comprising, based on the total volume of the solvent mixture, from about 40% to about 75% of an alkane, from about 15% to about 50% of an alcohol and from about 2% to about 10% of water at a temperature of between about 0° C. to about 30° C.

The cyclic siloxane production process of the present invention is a high-yield process, and the present process produces cyclic siloxane mixtures that are highly concentrated with cyclic siloxanes having a narrow range of molecular weight distribution.

DETAILED DESCRIPTION OF THE INVENTION

The improved, high-yield process of the present invention for producing cyclic siloxanes comprises the steps of gradually adding a functional alkylsilane to a biphasic reaction solvent mixture comprising, based on the total volume of the solvent mixture, from about 40% to about 75%, preferably from about 50% to about 73%, more preferably from about 60% to about 70%, of an alkane; from about 15% to about 50%, preferably from about 20% to about 45%, more preferably from about 25% to about 35%, of an alcohol; and from about 2% to about 10%, preferably from about 4% to about 8%, more preferably from about 5% to about 8%, of water.

The present hydrolysis process is conducted at a temperature of between about 0° C. and about 30° C., preferably between about 5° C. and about 27° C., more preferably between about 10° C. and about 25° C. It has been found that conducting the present process at a temperature higher than the specified range facilitates the production of linear polysiloxanes.

The rate of addition of the functional alkylsilane can vary considerably depending upon the temperature to which the reaction is permitted to proceed and the means employed to maintain the temperature of the reaction mixture. The present hydrolysis reaction is an exothermic reaction, and, thus, a heat removing means, such as a heat-exchanger, is required to uniformly remove the reaction heat. Consequently, the rate of addition of the functional alkylsilane can be adjusted to commensurate the efficiency of the heat removing means employed in the process. In addition, it is important to provide a good mixing of the reaction mixture to ensure that the heat generated during the hydrolysis reaction is uniformly distributed and efficiently removed, and does not create heat concentration spots within the reaction mixture. The temperature uniformity of the reaction mixture is important since, as stated above, the production of linear polysiloxanes is promoted by a reaction environment that has a temperature higher than the specified range of the present invention. In addition, it is believed that a well-mixed reaction mixture facilitates the production of cyclic siloxane mixtures having a more uniform molecular weight distribution by allowing rapid equilibration of the products between the aqueous and organic phases.

The suitable functional alkylsilanes for use herein have the following formula:

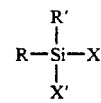

wherein R is an alkyl group containing from about 1 to about 5 carbon atoms, most preferred is methyl;

R' is hydrogen, a lower alkyl group containing from about 1 to about 5 carbon atoms or an alkenyl radical containing from about 1 to about 5 carbon atoms, most preferred is hydrogen; and X and X' are independently selected from the group consisting of halogens, including chlorine, bromine and iodine, and alkoxy units, including methoxy and ethoxy, most preferred X and X' are chlorines.

The suitable alkanes for the present invention are alkanes having about 5 to about 20 carbon atoms. Of these, preferred are pentane, hexane, heptane, octane, nonane, decane, undecane and dodecane; more preferred are pentane, hexane, heptane, octane, nonane and decane; most preferred are pentane, hexane and heptane. It has been found that cyclic alkane solvents are not particularly suited for use herein in that the use of a cyclic alkane as a reaction solvent promotes the production of linear polysiloxanes.

The suitable alcohols for use herein are alcohols having about 1 to about 20 carbon atoms. Preferred alcohols include methanol, ethanol, n-propanol, isopropanol, n-butanol, sec-butanol, tert-butanol, n-pentanol, tert-pentanol, neopentanol and n-hexanol. More preferred are methanol, ethanol, n-propanol, isopropanol, n-butanol, sec-butanol, tert-butanol, n-pentanol and tertpentanol. Most preferred are methanol, ethanol, n-propanol, isopropanol, n-butanol and tert-butanol.

The production process for cyclic siloxane of the present invention produces a mixture of cyclic siloxanes having the following formula:

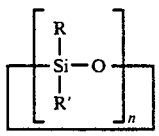

wherein the repeating unit n is between about 3 and about 25.

The cyclic siloxanes produced in accordance with the present invention are collected from the organic phase of the reaction mixture in accordance with any known extraction methods in the art. Illustrative examples of such suitable methods are vacuum distillation and liquid phase chromatography.

The present process is an improved process that produces a mixture of cyclic siloxanes having a much higher concentration of cyclic siloxanes having from about 4 to about 7 repeating units, as well as results in a higher production yield of cyclic siloxanes than the prior art processes. In addition, the present invention is a flexible process that can easily be modified to produce high concentrations of linear polysiloxanes since, as discussed above, employing cyclic alkane solvents and conducting the present process at an elevated temperature promote the production of linear polysiloxanes.

The following non-limiting examples are provided for illustration purposes and are not provided to limit the scope of the present invention thereto.

EXAMPLES

EXAMPLES 1-3

Synthesis of hydromethylcyclosiloxane in Hexane/Methanol/Water mixtures

EXAMPLE 1

540 ml (30 moles) of distilled water, 2260 ml (55.8 moles) of methanol, 5300 ml (40.6 moles) of hexane were charged into a 12000 ml 3-neck round bottom flask equipped with condenser, addition funnel, mechanical stirrer, thermometer, two thermocouples, nitrogen purge, sodium bicarbonate trap, strip chart recorder, and a temperature regulated cooling bath. 900 ml (8.45 moles) of dichloromethylsilane (DCMS) was charged into the addition funnel. The reaction mixture was cooled to and maintained at 20°±1° C. with vigorous stirring and the addition of DCMS was carried out over a period of 4 hours. Thereafter, the reaction mixture was maintained at 20°±1° C. for one additional hour, and then the reaction mixture was transferred to a separatory funnel to remove the aqueous phase. The resulting organic phase was washed twice with 2000 ml of 5.0% sodium bicarbonate solution, and twice with 2000 ml of distilled water. The organic phase was dried over sodium sulfate, filtered and concentrated under vacuum.

The concentrated organic phase was chemically analyzed to determine its contents using a vacuum distillation fractionation method, and the yields of the total hydromethylsiloxanes and hydromethylcyclosiloxanes (HMCS) produced were determined. The results are shown in Table below.

The composition of the HMCS was further analyzed by gas chromatography and was found to be 25.63% tetramer (D4), 40.49% pentamer (D5), 17.57% hexamer (D6), 4.57% heptamer (D7), 1.71% octamer (D8), 0.99% nonamer (D9), 0.68% decamer (D10), 0.54% undecamer (D11), 0.47% dodecamer (D12), 0.43% tridecamer (D13), 0.41% tetradecamer (D14), 0.36% pentadecamer (D15), 0.33% hexadecamer (D16), and 0.22% heptadecamer (D17).

EXAMPLE 2

Example 1 was repeated except 3875 ml (31.4 moles) of hexane was used.

The chemical analysis results are shown in Table, and the HMCS was found to be 24.72% D4, 44.31% D5, 18.39% D6, 4.77% D7, 1.78% D8, 1.00% D9, 0.67% D10, 0.51% D11, 0.41% D12, 0.37% D13, 0.32% D14, 0.25% D15, 0.19% D16, and 0.10%, D17.

EXAMPLE 3

Example 1 was repeated except 2650 ml (20.9 moles) of hexane was used.

The chemical analysis results are shown in Table, and the HMCS was found to be 24.77% D4, 43.10% D5, 18.47% D6, 5.09% D7, 2.08% D8, 1.26% D9, 0.91% D10, 0.74% D11, 0.63% D12, 0.61% D13, 0.52% D14, 0.44% D15, 0.34% D16, and 0.22% D17.

EXAMPLES 4-10

Synthesis of hydromethylcyclosiloxane in Pentane/Methanol/Water

EXAMPLE 4

Using 540 ml (30 moles) of distilled water, 2260 ml (55.8 moles) of methanol, 3975 ml (34.5 moles) of pentane and 880 ml (8.5 moles) of DCMS, the reaction procedure outline in Example 1 was repeated, except the reaction temperature was maintained at 15°±1° C. and the addition of DCMS was carried out over a period of 4.25 hours.

The chemical analysis results are shown in Table, and the HMCS was found to be 25.63% tetramer (D4), 40.49% pentamer (D5), 17.57% hexamer (D6), 4.57% heptamer (D7), 1.7% octamer (D8), 0.99% nonamer (D9), 0.68% decamer (D10), 0.54% undecamer (D11), 0.47% dodecamer (D12), 0.43% tridecamer (D13), 0.41% tetradecamer (D14), 0.36% pentadecamer (D15), 0.33% hexadecamer (D16), and 0.22% heptadecamer (D17).

EXAMPLE 5

The procedure outlined in Example 4 was repeated except 5300 ml (46.0 moles) of pentane was charged into the flask, 900.0 ml (8.645 moles) of DCMS was charged over a period of 4 hours, and the reaction temperature was maintained at 20°±1° C.

The chemical analysis results are shown in Table, and the HMCS was found to be 31.92% D4, 41.95% D5, 14.90% D6, 4.01% D7, 1.63% D8, 0.94% D9, 0.64%

D10, 0.49% D11, 0.39% D12, 0.31% D13, 0.24% D14, 0.19% D15, 0.13% D16, 0.10% D17, and 0.07% D18.

EXAMPLE 6

Example 5 was repeated except DCMS was added over a period of 4.25 hours.

The chemical analysis results are shown in Table, and the HMCS was found to be composed of 24.98% D4, 45.19% D5, 17.51% D6, 4.49% D7, 1.66% D8, 1.51% D9, 0.57% D10, 0.41% D11, 0.33D12, 0.24% D13, 0.22% D14, 0.17% D15, 0.11% D16, and 0.08% D17.

EXAMPLE 7

Example 6 was repeated except 1800 ml (17.3 moles) of DCMS was added.

The chemical analysis results are shown in Table, and the HMCS was found to be 26.37% D4, 41.57% D5, 16.29% D6, 4.76% D7, 2.00% D8, 1.25% D9, 0.95% D10, 0.77% D11, 0.68% D12, 0.61% D13, 0.55% D14, 0.49% D15, 0.43% D16, and 0.37% D17.

EXAMPLE 8

Example 6 was repeated except 1350 ml (13.0 moles) of DCMS was added.

The chemical analysis results are shown in Table, and the HMCS was found to be 31.32% D4, 43.61% D5, 14.99% D6, 3.50% D7, 1.27% D8, 0.73% D9, 0.54% D10, 0.44% D11, 0.38% D12, 0.33% D13, 0.29% D14, 0.25% D15, 0.20% D16, and 0.17% D17.

EXAMPLE 9

Example 6 was repeated except 900 ml (8.6 moles) of DCMS was added.

The chemical analysis results are shown in Table, and the HMCS was found to be 31.32% D4, 43.61% D5, 14.99% D6, 3.50% D7, 1.27% D8, 0.73% D9, 0.54% D10, 0.44% D11, 0.38% D12, 0.33% D13, 0.29% D14, 0.25% D15, 0.20% D16, and 0.17% D17.

EXAMPLE 10

Example 9 was repeated except 270 ml (15 moles) of distilled water, 1130 ml (27.9 moles) of methanol and 2650 ml (23.0 moles) of pentane were charged into the flask.

The chemical analysis results are shown in Table, and the HMCS was found to be 29.53% D4, 41.40% D5, 15.33% D6, 4.14% D7, 1.76% D8, 1.11% D9, 0.84% D10, 0.69% D11, 0.60% D12, 0.53% D13, 0.48% D14, 0.42% D15, 0.36% D16, and 0.30% D17.

EXAMPLE 11

Synthesis of hydromethylcyclosiloxane in Pentane/Ethanol/Water

The procedure outlined in Example 5 was repeated except a reaction solvent mixture of 540.0 ml (30.00 moles) of distilled water, 2260 ml (38.5 moles) of ethanol, 3975 ml (34.5 moles) of pentane were utilized.

The chemical analysis results are shown in Table, and the HMCS was found to be 25.45% D4, 41.70% D5, 17.21% D6, 5.18% D7, 2.26% D8, 1.37% D9, 0.98% D10, 0.77% D11, 0.64% D12, 0.54% D13, 0.45% D14, 0.38% D15, 0.32% D16, and 0.27% D17.

EXAMPLE 12

Synthesis of hydromethylcyclosiloxane in Pentane/iso-Propanol/Water

Example 11 was repeated except iso-propanol was used in place of ethanol.

The chemical analysis results are shown in Table, and the HMCS was found to be 24.64% D4, 40.25% D5, 17.39% D6, 5.71% D7, 2.67% D8, 1.69% D9, 1.26% D10, 0.98% D11, 0.80% D12, 0.67% D13, 0.56% D14, 0.45% D15, 0.37% D16, and 0.30% D17.

EXAMPLE 13

Synthesis of hydromethylcyclosiloxane in Pentane/tert-Butanol/Water:

Example 12 was repeated except tert-butanol was used in place of iso-propanol.

The chemical analysis results are shown in Table, and the HMCS was found to be 28.03% D4, 39.05% D5, 16.09% D6, 5.23% D7, 2.48% D8, 1.59% D9, 1.19% D10, 0.95% D11, 0.77% D12, 0.64% D13, 0.53% D14, 0.44% D15, 0.36% D16, and 0.30% D17.

COMPARATIVE EXAMPLE 1:

Synthesis of Hydromethylcyclosiloxane in Toluene/Methanol/Water:

Example 3 was repeated using 2650 ml (24.935 moles) of toluene in place of hexane.

The chemical analysis results are shown in Table, and the HMCS was found to be 3.96% D4, 25.52% D5, 25.52% D6, 9.04% D7, 4.50% D8, 3.12% D9, 2.42% D10, 2.02% D11, 1.74% D12, 1.52% D13, 1.31% D14, 1.05% D15, 0.81% D16, 0.57% D17 and 0.35% D18.

COMPARATIVE EXAMPLE 2

Synthesis of Hydromethylcyclosiloxane in Acetone/Water 400 ml (22.2 moles) of distilled water, 400 ml (5.4 moles) of acetone were charged into the 2000 ml 3-neck round bottom flask. 400 ml (3.8 moles) of DCMS was charged into the addition funnel. The reaction mixture was cooled to 20°±1° C. with vigorous stirring and the addition of DCMS was carried out over a period of 3 Hours, reaction temperature maintained at 20°±1° C. during addition. The reaction was maintained at 20°±1° C. for one additional hour. Immediately, 1.0 liter of hexane was added to the reaction mixture and then transferred to a separatory funnel. The aqueous phase was removed, and the organic phase was washed four times with 1000 ml of 5.0% sodium bicarbonate solution, and thrice with 1000 ml of distilled water. The organic phase was dried over sodium sulfate, filtered and concentrated under vacuum.

The chemical analysis results are shown in Table, and the HMCS was found to be 5.48% D4, 13.55% D5, 19.75% D6, 5.19% D7, 8.43% D8, 4.26% D9, 3.68% D10, 2.88% D11, 3.06% D12, 3.17% D13, 3.29% D14, 2.83% D15, 2.82% D16, and 0.50% D17.

COMPARATIVE EXAMPLE 3

Synthesis of Hydromethylcyclosiloxane in Methanol/Water

Comparative Example 2 was repeated except 400 ml (22.2 moles) of distilled water, and 400 ml (9.9 moles) of methanol were used.

The chemical analysis results are shown in Table, and the HMCS was found to be composed of 21.75% D4, 37.14% D5, 20.39% D6, 7.25% D7, 3.24% D8, 1.94% D9, 1.46% D10, 1.18% D11, 1.06% D12, 0.98% D13, 0.89% D14, 0.81% D15, 0.72% D16, and 0.65% D17.

TABLE

| Example | Total Hydromethylsiloxane Yield | HMCS Yield |
|---|---|---|
| 1 | 78.3% | 79.6% |
| 2 | 97.3% | 78.4% |
| 3 | 100% | 63.2% |
| 4 | 82.4% | 89.9% |
| 5 | 77.5% | 81.9% |
| 6 | 91.2% | 89.0% |
| 7 | 70.8% | 59.6% |
| 8 | 72.9% | 81.0% |
| 9 | 76.5% | 91.5% |
| 10 | 64.3% | 72.4% |
| 11 | 80.7% | 84.4% |
| 12 | 82.1% | 85.7% |
| 13 | 80.8% | 86.1% |
| C1 | 92.1% | 47.7% |
| C2 | 84.9% | 16.8% |
| C3 | 73.6% | 17.2% |

As can be seen from the above examples, the cyclic siloxane production process of the present invention, which utilizes a biphasic reaction solvent mixture, is an improved process for the production of cyclic siloxanes and produces a higher concentration of cyclic siloxane mixtures having a narrow range of molecular weight distribution over the prior art processes. Furthermore, the present process is not an energy intensive process, unlike many of the prior art teachings and practices, since the reaction is readily carried out in ambient temperatures.

What is claimed is:

1. An improved, high-yield process for producing cyclic siloxanes comprising the steps of gradually mixing a functional alkylsilane to a well-blended biphasic reaction solvent mixture comprising, based on the total volume of the solvent mixture, from about 40% to about 75% of an alkane, from about 15% to about 50% of an alcohol and from about 2% to about 10% of water at a temperature of between about 0° C. to about 30° C.

2. The process for producing cyclic siloxanes according to claim 1, wherein said functional alkylsilane has the following formula:

wherein

R is an alkyl group containing from 1 to 5 carbon atoms,

R', is hydrogen, a lower alkyl group containing from 1 to 5 carbon atoms or an alkenyl radical, and X and X' are independently selected from the group consisting of halogens and alkoxy units.

3. The process for producing cyclic siloxanes according to claim 1, wherein said alkane is an aliphatic alkane having about 5 to about 20 carbon atoms.

4. The process for producing cyclic siloxanes according to claim 1, wherein said alkane is selected from the group consisting of pentane, hexane, heptane, octane, nonane, decane, undecane and dodecane.

5. The process for producing cyclic siloxanes according to claim 1, wherein said alkane is selected from the group consisting of pentane, hexane and heptane.

6. The process for producing cyclic siloxanes according to claim 1, wherein said alcohol is an alcohol having about 1 to about 20 carbon atoms.

7. The process for producing cyclic siloxanes according to claim 1, wherein said alcohol is selected from the group consisting of methanol, ethanol, n-propanol, isopropanol, n-butanol, sec-butanol, tert-butanol, n-pentanol, tert-pentanol, neopentanol and n-hexanol.

8. The process for producing cyclic siloxanes according to claim 1, wherein said alcohol is selected from the group consisting of methanol, ethanol, n-propanol, isopropanol, n-butanol and tert butanol.

9. The process for producing cyclic siloxanes according to claim 1, wherein said reaction solvent mixture comprises from about 60% to about 70% of an alkane.

10. The process for producing cyclic siloxanes according to claim 1, wherein said reaction solvent mixture comprises from about 25% to about 35% of an alcohol.

11. The process for producing cyclic siloxanes according to claim 1, wherein said reaction solvent mixture comprises from about 5% to about 8% of water.

12. The process for producing cyclic siloxanes according to claim 1, wherein said process is conducted at a temperature of between about 10° C. and about 25° C.

13. The process for producing cyclic siloxanes according to claim 2, wherein R is methyl group.

14. The process for producing cyclic siloxanes according to claim 2, wherein R' is hydrogen.

15. The process for producing cyclic siloxanes according to claim 2, wherein X and X' are independently selected from the group consisting of chlorine, bromine and iodine.

16. The process for producing cyclic siloxanes according to claim 2, wherein X and X' are independently selected from the group consisting of methoxy and ethoxy units.

17. The process for producing cyclic siloxanes according to claim 2, wherein X and X' are chlorines.

18. The process for producing cyclic siloxanes according to claim 1, wherein said functional alkylsilane is dichloromethylsilane.

* * * * *